United States Patent [19]

Moore

[11] 3,956,505
[45] May 11, 1976

[54] INSECTICIDAL BIS-PHENYLHYDRAZONE SULFIDES

[75] Inventor: Joseph E. Moore, Richmond, Calif.

[73] Assignee: Chevron Research Company, San Francisco, Calif.

[22] Filed: Jan. 27, 1975

[21] Appl. No.: 544,149

Related U.S. Application Data

[62] Division of Ser. No. 470,482, May 16, 1974, Pat. No. 3,867,450.

[52] U.S. Cl. .............................................. 424/327
[51] Int. Cl.² ...................... A01N 9/20; A01N 9/24
[58] Field of Search ................. 424/327; 260/566 B

[56] References Cited
UNITED STATES PATENTS
3,826,844   7/1974   Moon.................................. 424/327

OTHER PUBLICATIONS
Moon et al., J. Agr. Food Chem., Vol. 20, pp. 888–891, (1972).
Chem. Abst., 77, 88470(b), (1972), Moon et al.

*Primary Examiner*—Stanley J. Friedman
*Assistant Examiner*—D. W. Robinson
*Attorney, Agent, or Firm*—G. F. Magdeburger; D. A. Newell; Raymond Owyang

[57] ABSTRACT

Bis-phenylhydrazone sulfides of the formula

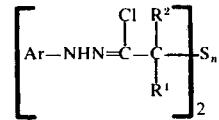

wherein R¹ and R² individually are hydrogen or alkyl, Ar is phenyl or substituted phenyl, and *n* is 1, 2 or 3, have morphogenetic hormonal mimetic insecticidal activity.

14 Claims, No Drawings

INSECTICIDAL BIS-PHENYLHYDRAZONE SULFIDES

This a division of application Ser. No. 470,482, filed May 16, 1974, now U.S. Pat. No. 3,867,450.

BACKGROUND OF INVENTION

1. Field of the Invention

The present invention is concerned with insecticidal compounds which have morphogenetic hormonal mimetic activity. Compounds having morphogenetic hormonal mimetic activity exert a disrupting influence upon the normal development of insects. These compounds interfere with the normal metamorphosis of the pest insects and result in the formation of individual insects of the treated species which develop abnormally and are nonviable or sterile. This ultimately leads, indirectly at least, to the destruction of the insect population.

2. Description of the Prior Art

Thioketal-substituted phenylhydrazones are disclosed by M. W. Moon et al. "J. Agr. Food Chem.", 20, 888 (1972). German Patent No. 2,157,601 [C. A. 77 88470b (1972)] also disclose thio-substituted phenylhydrazones. Phenylhydrazone compounds are also disclosed in "J. Agr. Food Chem.", 20, 1187 (1972); "J. Org. Chem.", 37, 383, 386, 2005 (1972); and Netherlands patent application No. 7,113,497.

DESCRIPTION OF THE INVENTION

The insecticidal bis-phenylhydrazone sulfides of the invention are represented by the formula

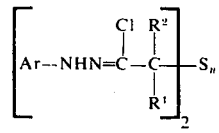

wherein $R^1$ is hydrogen or alkyl of 1 to 6 carbon atoms, $R^2$ is hydrogen or alkyl of 1 to 6 carbon atoms and Ar is phenyl substituted with up to 5 (0 to 5), preferably up to 3 (0 to 3), fluoro, chloro or bromo, or with up to 2 (0 to 2), preferably up to 1 (0 to 1), nitro groups.

The preferred $R^1$ group is hydrogen or alkyl of 1 to 3 carbon atoms. The preferred $R^2$ group is alkyl of 1 to 3 carbon atoms. The preferred Ar group is phenyl substituted up to 5 chloro or bromo, especially trichlorophenyl.

Representative compounds of formula I wherein $n$ is 1, 2 or 3 are tabulated in Table I ($\phi$ represents phenyl).

TABLE I

| Ar | $R^1$ | $R^2$ |
|---|---|---|
| $\phi$ | H | H |
| 2,4-$Cl_2\phi$ | H | H |
| m-$O_2N\phi$ | H | H |
| $\phi$ | H | $CH_3$ |
| 3,5-$Cl_2\phi$ | H | $C_2H_5$ |
| 2,4,6-$Cl_3\phi$ | H | n-$C_3H_7$ |
| 3,5-$F_2\phi$ | H | sec-$C_4H_9$ |
| 2,4,6-$Br_3\phi$ | H | n-$C_5H_{11}$ |
| 2,4,6-$Cl_3\phi$ | H | n-$C_6H_{13}$ |
| 3,5-$Cl_2\phi$ | $CH_3$ | $CH_3$ |
| 2,4,6-$Cl_3\phi$ | $CH_3$ | $CH_3$ |
| 2,4-$(O_2N)_2\phi$ | $CH_3$ | $CH_3$ |
| 2,6-$Cl_2$—4$Br\phi$ | $C_2H_5$ | $C_2H_5$ |
| 2,4,6-$Cl_3\phi$ | n-$C_6H_{13}$ | $CH_3$ |

A preferred class of bis-phenylhydrazone sulfides of formula (I) are those wherein $R^1$ is hydrogen; $R^2$ is alkyl of 1 to 6 carbon atoms, more preferably 1 to 3 carbon atoms; and Ar is phenyl substituted with up to 3 fluoro, chloro or bromo, more preferably phenyl substituted with up to 3 chloro or bromo.

Another preferred class of bis-phenylhydrazone sulfides of formula (I) are those wherein $R^1$ or $R^2$ individually are alkyl of 1 to 6 carbon atoms, preferably 1 to 3 carbon atoms, and Ar is phenyl substituted with up to 3 fluoro, chloro or bromo, more preferably phenyl substituted with up to 3 chloro or bromo.

The compounds of the invention are prepared by reacting a bisalkanoyl acid chloride (II) with a phenylhydrazine (III) and then reacting the resulting bishydrazide (IV) with phosphorus pentachloride, as depicted in reactions (1) and (2):

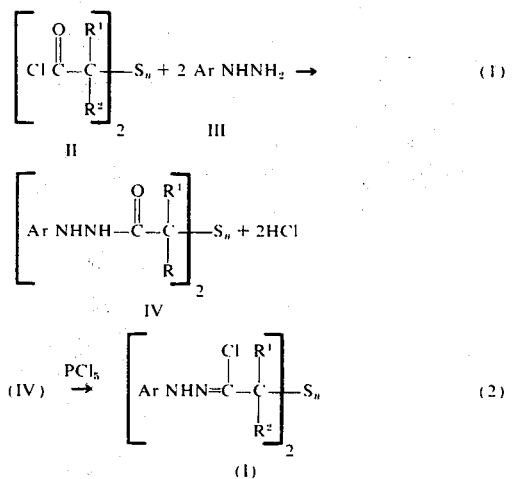

wherein $R^1$, $R^2$, Ar and $n$ have the same significance as previously defined.

Reaction (1) is conducted by reacting about 2 mols of the phenylhydrazine (I) with about 1 mol of the bisalkanoyl acid chloride in the presence of about 2 mols of an acid acceptor in an inert solvent at a temperature of from about 0° to 50°C, by more or less conventional procedures. Suitable acid acceptors are trialkylamines, such as triethylamine, or pyridine compounds, such as pyridine or alpha-picoline.

Reaction (2) is conducted by reacting about 1 mol of the bishydrazide (IV) with about 2 mols of phosphorus pentachloride in the presence of an inert solvent at a temperature of about 25° to 100°C, and then working up the product mixture with phenol. Suitable inert solvents are chlorinated hydrocarbons such as carbon tetrachloride and methylene dichloride. Reaction (2) is a known reaction for the chlorination of hydrazides, as disclosed in Netherlands application No. 7,113,497.

The compounds of the invention are useful as morphogenetic hormonal mimetic insecticides, particularly against insects such as cabbage looper larvae and alfalfa weevil larvae.

The compounds are very potent and are used at extremely low concentrations. For example, compositions containing 100 ppm to 0.01 ppm, preferably from 5 ppm to 0.1 ppm, are effective for inhibiting or interfering with the normal metamorphosis of insects. However, the effective concentration depends in part on the mode of application and the particular insect.

The compounds may be applied in either liquid or solid formulations to the pre-adult insects or their habitats. For example, they may be sprayed or otherwise applied directly to plants or aqueous bodies so as to effect control of insects coming into contact therewith.

Formulations of the compounds of this invention will comprise a metamorphosis inhibiting amount of one or more of the compounds and a biologically inert carrier. Usually they will also contain a wetting agent. Solid carriers such as clay, talc, sawdust, alfalfa meal, and the like may be used in such formulations. Liquid diluents which may be used with these compounds include water, aliphatic and aromatic solvents. In addition, these formulations may contain other compatible pesticides, fillers, stabilizers, attractants and the like.

The concentration of the active ingredient to be used with inert carriers, either solid or liquid carriers, will be dependent upon many factors, such as the particuular compound which is used, the carrier in or upon which it is incorporated, the method and conditions of application, the insect species to be controlled, etc., the proper consideration of these factors being within the skill of those versed in the art. In general, the toxic ingredients of this invention will be effective in concentrations from about 0.0001% by weight to as high as 50% by weight or higher.

The terms "insecticide" and "insect" as used herein refer to their broad and commonly understood usage rather than to those creatures which in the strict biological sense are classified as insects. Thus, the term insect is used not only to include small invertebrate animals belonging to the class Insecta but also to other related classes of arthropods whose members are segmented invertebrates having more or fewer than six legs, such as spiders, mites, ticks, centipedes, worms and the like.

EXAMPLE 1

Preparation of the bis-phenylhydrazone of 2,2'-dithiobisisobutyryl chloride

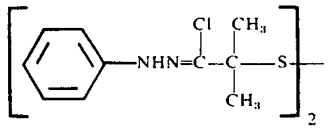

A solution of 14.4 g. 2,2'-dithiobisisobutyric acid (Chem. Abs. 64, 6635b) and 40 ml thionyl chloride was stirred and refluxed for 1 hour. The excess thionyl chloride was removed by evaporation under reduced pressure. The resulting acid chloride product was diluted with 30 ml methylene chloride and added over a 20-minute period to a cooled solution of 13.1 g. phenylhydrazine, 13.5 g. triethylamine and 150 ml glyme. The reaction was then diluted with 300 ml water and extracted with methylene chloride. The methylene chloride extracts were dried over magnesium sulfate and evaporated to give a dark solid. The solid was recrystallized from hexane-benzene to give 11.3 g. of 2,2'-dithiobisisobutyric acid bis-phenylhydrazide, as a beige solid, m.p. 144°C. Elemental analysis for $C_{20}H_{26}N_4O_2S_2$ showed: S% calc. 15.3; found 13.7.

A solution of 9.4 g. 2,2'-dithiobisisobutyric acid bis-hydrazide, 10.0 g. phosphorus pentachloride and 100 ml carbon tetrachloride was stirred and refluxed for 5 hours. The solution was then colled and added over 20 minutes to a solution of 13.5 g. phenol in 100 ml. carbon tetrachloride. Finally, 100 ml ethanol was added to the reaction mixture. The reaction mixture was then stripped to give 19 g. of an oil. The oil was chromatographed on silica gel (benzene eluant) to give 6.0 g. of the product, as a viscous red oil. Elemental analysis for $C_{20}H_{24}Cl_2N_4S_2$ gave: %S, calc. 14.08; found 13.3; %Cl, calc. 15.5, found 14.8.

The above chlorination reaction with phosphorus pentachloride is similar to that described in Netherlands patent application No. 7,113,497.

EXAMPLE 2

Bis-2,4,6-trichlorophenylhydrazone of 2,2'-dithiobisisobutyryl chloride

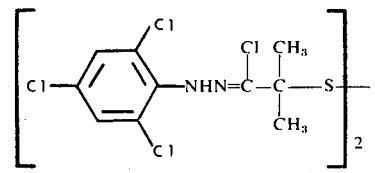

This product was prepared by a procedure similar to that of Example 1. The product is a white solid, m.p. 123°–124°C. Elemental analysis for $C_{20}H_{18}Cl_8N_4S_2$ gave: %S calc. 9.7, found 10.1; %Cl calc. 42.8; found 43.1.

EXAMPLE 3

Bis-phenylhydrazone of 2,2'-dithiobispropionyl chloride

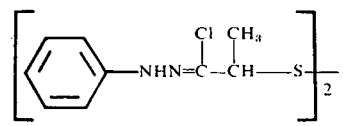

This product was prepared by a procedure similar to that of Example 1. The product is a viscous red oil. Eleemental analysis for $C_{18}H_{20}Cl_2N_4S_2$ gave: %S, calc. 15.0, found 13.6; %Cl calc. 16.6, found 15.5.

EXAMPLE 4

Bis-p-nitrophenylhydrazone of 2,2'-dithiobispropionyl chloride

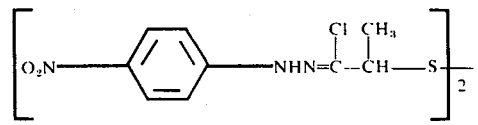

This product was prepared by a procedure similar to that of Example 1. The product is a yellow solid (m.p. ca 80°C) which forms selectively stable complexes with solvents such as benzene and chloroform.

EXAMPLE 5

Cabbage Looper Control

The compounds of Example 1–3 were tested as juvenile hormonal mimetic insecticides against cabbage looper (*Trichoplusia ni*) by the following procedure: 5 microliters of an acetone solution containing 100 micrograms of the test compound were applied topically to the entire length of the body of a late-fifth-stage cabbage looper larva. Normally 10 larvae were treated per test. The treated larvae were then fed until they pupated. The pupae were then incubated until the adult emerged. The mortality of the pupae and adults were determined. The compounds tested and the total pupal and adult mortality are tabulated in Table II.

EXAMPLE 6

Alfalfa Weevil Control

The compounds of Examples 1-3 were tested as juvenile hormonal mimetic insecticides against alfalfa weevils (*Haperapostica, Gyllenhal*) by the same procedure employed for cabbage looper, except that 5 micrograms of test compound were applied to last-stage alfalfa weevil larvae. The compounds tested and th total pupal and adult mortality are tabulated in Table II.

TABLE II

| Compound of Example No. | Insect | % Mortality |
|---|---|---|
| 1 | Cabbage Looper | 100 |
| 2 | " | 40 |
| 3 | " | 100* |
| 1 | Alfalfa Weevil | 100* |
| 2 | " | 10 |
| 3 | " | 100* |

*1 microgram of test compound.

What is claimed is:

1. A method of controlling insects selected from the group consisting of cabbage looper larvae and alfalfa weevil larvae which comprises contacting said pre-adjult insects with a metamorphosis disrupting effective amount of a compound of the formula

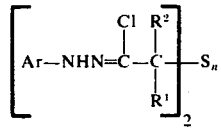

wherein $R^1$ and $R^2$ individually are hydrogen or alkyl of 1 to 6 carbon atoms, Ar is phenyl substituted with up to 5 fluoro, chloro or bromo groups or with up to 2 nitro groups and $n$ is 1, 2, or 3.

2. The method of claim 1 wherein $R^1$ is hydrogen, $R^2$ is alkyl of 1 to 3 carbon atoms and Ar is phenyl substituted with up to 5 chloro or bromo groups.

3. The method of claim 2 wherein Ar is phenyl substituted with up to 3 chloro groups and n is 2.

4. The method of claim 3 wherein $R^2$ is methyl and Ar is phenyl.

5. the method of claim 1 wherein $R^1$ is alkyl of 1 to 3 carbon atoms, $R^2$ is alkyl of 1 to 3 carbon atoms and Ar is phenyl substituted with up to 5 chloro or bromo groups.

6. The method of claim 5 wherein Ar is phenyl substituted with up to 3 chloro groups and $n$ is 2.

7. The method of claim 6 wherein $R^1$ and $R^2$ are methyl and Ar is phenyl.

8. The method of claim 6 wherein $R^1$ and $R^2$ are methyl and Ar is 2,4,6-trichlorophenyl.

9. A composition useful for the control of insects comprising a metamorphosis disrupting effective amount of a compound of the formula

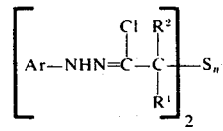

wherein $R^1$ and $R^2$ individually are hydrogen or alkyl of 1 to 6 carbon atoms, Ar is phenyl substituted with up to 5 fluoro, chloro or bromo groups or with up to 2 nitro groups and $n$ is 1, 2 or 3, and a biologically inert carrier.

10. The composition of claim 9 wherein $R^1$ is hydrogen, $R^2$ is alkyl of 1 to 3 carbon atoms and Ar is phenyl substituted with up to 5 chloro or bromo groups.

11. The composition of claim 10 wherein Ar is phenyl substituted with up to 3 chloro groups and $n$ is 2.

12. The composition of claim 9 wherein $R^1$ is alkyl of 1 to 3 carbon atoms, $R^2$ is alkyl of 1 to 3 carbon atoms and Ar is phenyl substituted with up to 5 chloro or bromo groups.

13. The composition of claim 12 wherein Ar is phenyl substituted with up to 3 chloro groups and $n$ is 2.

14. The composition of claim 13 wherein $R^1$ and $R^2$ are methyl and Ar is phenyl.

* * * * *